United States Patent
Yi et al.

(10) Patent No.: US 9,364,290 B2
(45) Date of Patent: Jun. 14, 2016

(54) STAND FOR A MEDICAL-OPTICAL INSTRUMENT

(71) Applicants: KOH YOUNG TECHNOLOGY INC., Seoul (KR); INDUSTRY-UNIVERSITY COOPERATION FOUNDATION HANYANG UNIVERSITY ERICA CAMPUS, Ansan-si, Gyeonggi-do (KR)

(72) Inventors: Byung-Ju Yi, Bucheon-si (KR); Jong-Tae Seo, Ansan-si (KR)

(73) Assignees: KOH YOUNG TECHNOLOGY INC., Seoul (KR); INDUSTRY-UNIVERSITY COOPERATION FOUNDATION HANYANG UNIVERSITY ERICA CAMPUS, Ansan-Si, Gyeonggi-Do (KR)

( * ) Notice: Subject to any disclaimer, the term of this patent is extended or adjusted under 35 U.S.C. 154(b) by 0 days.

(21) Appl. No.: 14/374,374

(22) PCT Filed: Feb. 18, 2014

(86) PCT No.: PCT/KR2014/001284
§ 371 (c)(1),
(2) Date: Jul. 24, 2014

(87) PCT Pub. No.: WO2014/129778
PCT Pub. Date: Aug. 28, 2014

(65) Prior Publication Data
US 2015/0342692 A1  Dec. 3, 2015

(30) Foreign Application Priority Data
Feb. 19, 2013 (KR) .................. 10-2013-0017327

(51) Int. Cl.
A47F 5/00 (2006.01)
A47F 7/00 (2006.01)
(Continued)

(52) U.S. Cl.
CPC ............. *A61B 19/26* (2013.01); *A61B 19/5202* (2013.01); *A61B 19/5223* (2013.01);
(Continued)

(58) Field of Classification Search
CPC ............... A61B 19/26; A61B 19/5223; A61B 2019/264; F16M 11/2092; F16M 11/38; F16M 11/2042

USPC ...................................................... 248/123.11
See application file for complete search history.

(56) References Cited

U.S. PATENT DOCUMENTS 3,762,796 A * 10/1973 Heller .................... F16M 11/08
359/375
(Continued)

FOREIGN PATENT DOCUMENTS

| JP | 09-149877 | 6/1997 |
| JP | 2005-052679 | 3/2005 |

(Continued)

OTHER PUBLICATIONS

International Search Report for International Application No. PCT/KR2014/001284, dated May 29, 2014.
(Continued)

*Primary Examiner* — Mark Wendell
(74) *Attorney, Agent, or Firm* — Kile Park Reed & Houtteman PLLC

(57) ABSTRACT

A stand for medical optical instrument capable of easily extending, adjusting easily a counter balancing according to a change of a weight of medical optical instrument such as microscope, as well as, maintaining stably a counter balancing regardless of a position of medical optical instrument. The stand for medical optical instrument includes a first to fourth links having a first to fourth turning joins, wherein the first to fourth links are rotatably coupled to each other in a parallelogram shape and the second turning joint is rotatably coupled to a holding unit, a carrier arm extended from the fourth link; and a counter balancing unit coupled to the first and second links, wherein the counter balancing unit is rotated in connection with the first and second links on the second turning joint according to the rotation of the carrier arm, and capable of maintaining a counter balancing of the carrier arm by compensating a torque generated in the second turning joint according to a medical optical instrument installed on the front link.

7 Claims, 6 Drawing Sheets

(51) Int. Cl.
  *F16M 11/00* (2006.01)
  *F16M 13/00* (2006.01)
  *A61B 19/00* (2006.01)
  *F16M 11/20* (2006.01)
  *F16M 11/38* (2006.01)

(52) U.S. Cl.
  CPC ....... *F16M11/2042* (2013.01); *F16M 11/2092* (2013.01); *F16M 11/38* (2013.01); *A61B 2019/263* (2013.01); *A61B 2019/264* (2013.01); *A61B 2019/265* (2013.01)

(56) References Cited

U.S. PATENT DOCUMENTS

| | | | | |
|---|---|---|---|---|
| 3,891,301 A * | 6/1975 | Heller | ................... | F16M 11/08 359/384 |
| 4,339,100 A * | 7/1982 | Heller | ................... | F16M 11/08 248/123.2 |
| 5,205,522 A * | 4/1993 | Nakamura | ............ | F16M 11/04 248/123.11 |
| 5,213,293 A * | 5/1993 | Muentener | ............ | F16M 11/04 248/123.11 |
| 5,667,186 A * | 9/1997 | Luber | ................... | A61B 19/26 248/123.11 |
| 7,109,678 B2 * | 9/2006 | Kraus | ................... | A61B 19/26 248/280.11 |
| 7,189,246 B2 * | 3/2007 | Otsuka | ............... | A61B 19/0256 600/102 |
| 7,207,531 B2 * | 4/2007 | Piontkowski | .......... | A61B 19/26 248/122.1 |
| 7,556,626 B2 * | 7/2009 | Ueda | ..................... | A61B 19/26 600/102 |
| 8,006,850 B2 * | 8/2011 | Rotheisler | ............... | B66C 23/14 212/196 |
| 8,038,108 B2 * | 10/2011 | Yasunaga | ............... | A61B 19/26 248/123.2 |
| 8,746,634 B2 * | 6/2014 | Rotheisler | .......... | F16M 11/2085 248/123.2 |

FOREIGN PATENT DOCUMENTS

| | | |
|---|---|---|
| JP | 2008-086711 | 4/2008 |
| KR | 10-0149044 | 10/1998 |

OTHER PUBLICATIONS

Written Opinion with English Translation for International Application No. PCT/KR2014/001284, dated May 29, 2014.

* cited by examiner

STAND FOR A MEDICAL-OPTICAL INSTRUMENT

TECHNICAL FIELD

Exemplary embodiments of the present invention relate to a stand for a medical optical instrument. More particularly, exemplary embodiments of the present invention relate to a stand for a medical optical instrument which is installed on medical optical instrument such as a microscope and capable of moving and stopping to a desired position.

BACKGROUND ART

Microsurgery has been studied and introduced as a medical optical instrument in various surgeries which uses a surgical microscope to observe an affected area.

In such a microsurgery, a stand is required to install a surgical microscope which is a weight and accessory equipment such that the surgical microscope and the accessory equipment are stopped and maintained in a desired position.

In general, in such a stand, a center portion of a link unit is rotatably coupled to a holding unit using a parallel link, and at the same time, a surgical microscope is installed on one end portion of the link unit, and has a balanced structure having counterweight installed on one end portion of the surgical microscope to counterbalance a weight of the surgical microscope of another end portion of the surgical microscope around a rotating point.

Since accessories, such as an assistant scope or a video camera, are installed in a surgical microscope, an overall balance adjustment operation is carried out by changing a position of a counterweight according to its weight such that a balance between a surgical microscope and a counterweight is caught.

It is required to completely maintain a balance of both sides of a horizontal direction and a vertical direction of a surgical microscope to stop a surgical microscope and its accessories to a desired position, however, complete balance adjustment of both sides of a horizontal direction and a vertical direction of a surgical microscope of conventional stand is not performed easily.

DISCLOSURE

Technical Problem

Therefore, the technical problem of the present invention is to provide a stand for a medical optical instrument in which a counterbalancing adjustment according to a change of a weight of a medical optical instrument such as microscope is easy, and a stable counterbalancing is maintained regardless of a position of a medical optical instrument.

Technical Solution

According to an embodiment of the present invention, a stand for a medical optical instrument includes a carrier arm including a first to fourth links rotatably coupled in a parallelogram shape with a first to fourth turning joints, in which the second turning joint is rotatably installed on a holding unit and a front link is extended from the fourth link, and a counterbalancing unit coupled to the first and second links to rotate in connection with the first and second links on the second turning joint according to the rotation of a carrier arm, to maintain a counterbalancing of the carrier arm by compensating a torque generated in the second turning joint by a medical optical instrument installed on the front link according to the rotation of the carrier arm.

In one embodiment, the counterbalancing unit may include first and second balancing links which are extended from the first and second links, respectively, to rotate in connection with the first and second links on the second turning joint, and first and second counter weights installed on the first and second balancing links, respectively.

Herein, the first and second counter weights may be changed according to a weight of a medical optical instrument.

Also, the first and second counter weights may be installed on the first and second balancing links, respectively, to be replaceable according to a weight of the medical optical instrument.

Meanwhile, the stand for the medical optical instrument may further include a carrier arm for extension which is coupled to the carrier arm to extend a length of the carrier arm.

In one embodiment, the carrier arm for extension may include a base link portion rotatably coupled to the first and second tuning joints in a parallelogram shape, an extension link portion rotatably coupled to the base link portion and the front link of the carrier arm in a parallelogram shape, and a front link for extension extended from the extension link portion.

Meanwhile, the carrier arm for extension is capable of extending the carrier arm for N stages by rotatably coupling the N arms to each other, and at the same time, rotatably and sequentially coupling to the carrier arm.

In one embodiment, the carrier arm for extension may include a base link portion rotatably coupled to the first and second tuning joints of the carrier arm in a parallelogram shape, an extension link portion rotatably coupled to the base link portion and the front link of the carrier arm in a parallelogram shape, an additional link portion for extension rotatably coupled to the extension link portions of the remaining carrier arms except for the carrier arm for extension coupled to the carrier arm to a first order, the carrier arm for extension coupled to the carrier arm to an N-th order, in which N−1 carrier arms for extension are serially and rotatably coupled to the N-th carrier arm for extension coupled to the carrier arm, is rotatably coupled to the extension link portion, and a front link for extension extended from the extension link portion of the carrier arm which is coupled to the carrier arm to a first order and the additional link portion for extension of the remaining carrier arm for extension positioned at the most end portion.

Herein, except for a front link for extension of carrier arm for extension which is coupled to the carrier arm to a last order, a front link for extension of carrier arm for extension, which is coupled to carrier arm to an N-th order, is rotatably coupled to an additional link portion for extension of carrier arm for extension which is coupled to the carrier arm to N+1-th order.

Advantageous Effects

Thus, a stand for medical optical instrument is capable of installing first and second counter weights to be replaceable according to a weight of medical optical instrument which is installed on a carrier arm, as well as, easily adjusting a counter balance of weight according to a changed weight of a medical optical instrument by moving first and second counter weights in which first and second balancing links of carrier arm are rotated in connection with the medical optical instrument on a second turning joint when a position of a medical optical instrument is changed. And there is an effect of completely maintaining stable a counterbalancing in both sides, a horizontal direction and a vertical direction, regardless of a position of a medical optical instrument.

Also, even though a length of a stand is extended to a user's desired length by using carrier arms for extension, a front link of a carrier arm and front links for extension of the carrier arms for extension are organically coupled to adjacent carrier arms for extension and a movement of carrier arm positioned at the most end is transferred to first and second balancing links through passing first and second links of carrier arm, a position of the first and second counter weights are moved according to a changed position of a medical optical instrument, and therefore, a complete and stable counterbalancing on both sides, horizontal and vertical directions, is maintained regardless of a position of a medical optical instrument.

In other words, a length of a stand is easily extended to a user's desired length, as well as, easy counterbalancing and stably maintaining a counter balancing are capable when the length of the stand is extended.

MODE FOR INVENTION

Figure 1:
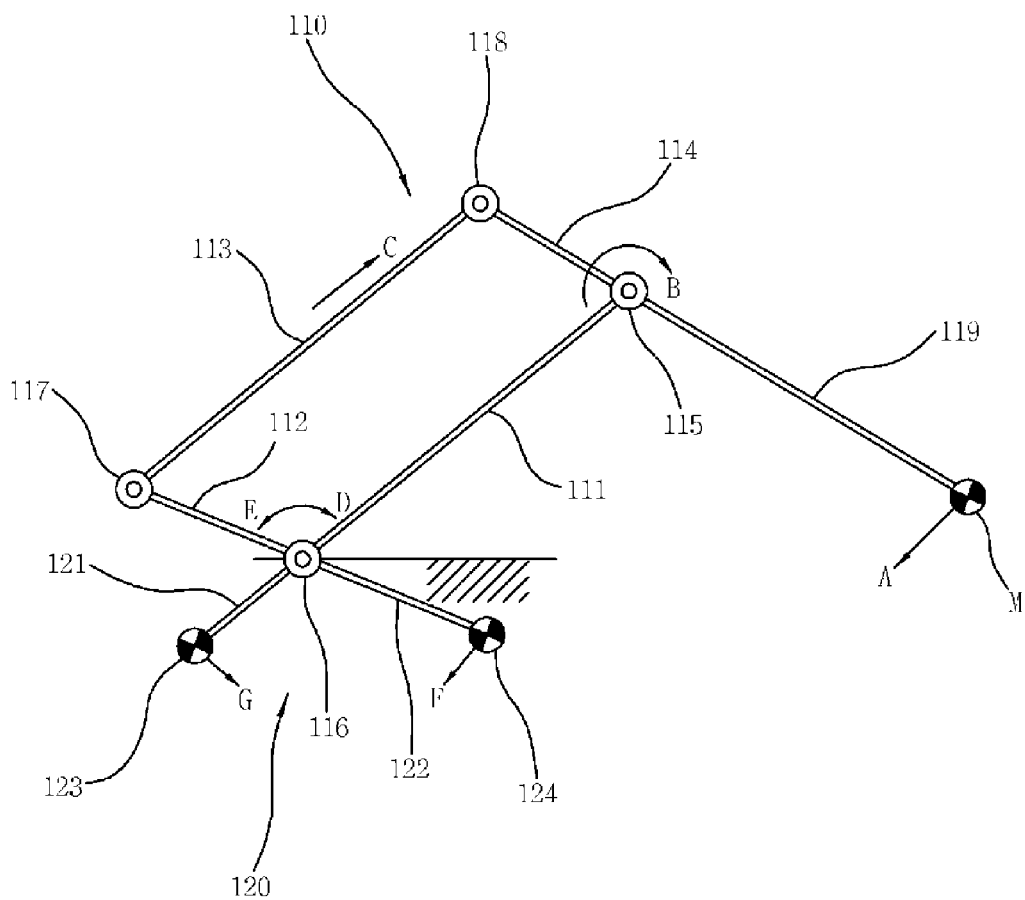
FIG. 1 is a schematic diagram of a stand according to an embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For convenience, same numerals are used for identical or similar elements of an apparatus of cutting a tempered substrate and the conventional one.

Hereinafter, with reference to the drawings, preferred embodiments of the present invention will be described in detail.

FIG. 1 is a schematic diagram of a stand according to an embodiment of the present invention.

Referring to FIG. 1, a stand 100 according to an exemplary embodiment of the present invention includes a carrier arm 110, and a counter balancing unit 120.

The carrier arm 120 is rotatably installed on a holding unit (not shown), a medical optical instrument M such as microscope may be installed on a fleet of the carrier arm 110. Herein, the medical optical instrument M may be rotatably coupled to the fleet of the carrier arm 110.

The carrier arm 110 may include a first to fourth links 111 112 113 and 114, a first to fourth turning joints 115 116 117 and 118, and a front link 119.

The first to the fourth links 111 112 113 and 114 may be coupled to each other in a parallelogram shape through the first to the fourth turning joints 115 116 117 and 118. In more detail, the first link 111 and the second link 112 are rotatably coupled by the second turning joint 116, the second link 112 and the third link 113 are rotatably coupled by the third turning joint 117, the third link 113 and the fourth link 114 are rotatably coupled by the fourth turning joint 118, the fourth link 114 and the first link 111 are rotatably coupled by the first turning joint 115, and therefore, the first to the fourth links may be rotatably coupled to each other by the first to the fourth turning joints 115 116 117 and 118.

And, any one of the first to fourth turning joints which couples the first to fourth links in a parallelogram shape may be rotatably coupled to the holding unit. For example, the second turning joint 116 may be rotatably coupled to the holding unit as shown in FIG. 1.

Meanwhile, the front link 119 may be extended from any one link selected among the first to fourth links 111 112 113 and 114. For example, when the second turning joint is rotatably coupled to the holding unit, the front link 119 may be extended from the fourth link 114.

The counter balancing unit 120 may be coupled to the first and second links 111 and 112. Therefore, the counter balancing unit 120 is capable of maintaining a counterbalancing of the carrier arm 110 by compensating a torque generated in the second turning joint 112 of a medical optical instrument M installed on the front link 119 since the counter balance unit 120 is rotated in connection with the first and second links 111 and 112 about the second turning joint 116 according to the rotation of the carrier arm 110.

The counter balancing unit 120 may include a first balancing link 121, a second balancing link 122, the first count weight 123, and a second count weight 124.

The first balancing link 121 is extended from the first link 111 to be parallel to the first link 111, and may be rotated in connection with the first link 111 on the second turning joint 116.

The second balancing link 122 is extended from the second link 112 to be parallel to the second link 112, and may be rotated in connection with the second link 112 on the second turning joint 116.

Meanwhile, although it is not shown in the figure, lengths of the first and second balancing links 121 and 122 may be changed according to a weight of the medical optical instrument M installed on the front link 119 of the carrier arm 110. Herein, lengths of the first and second balancing links 121 and 122 may be changed to be different to each other.

The first counter weight 123 may be installed on the first balancing link 121.

The second counter weight 124 may be installed on the second balancing link 122.

Herein, the first and second counter weights 123 and 124 may be installed on the first and second balancing links 121 and 122, respectively, such that they are replaced according to a weight of medical optical instrument M installed on the front link 119 of the carrier arm 110.

As described above, a brief description of a process to move a medical optical instrument M such as microscope installed on a stand 100 according to an embodiment of the present invention is explained below.

First, when the medical optical instrument M installed on the front link 119 is pulled to a direction of an arrow A, then the front link 119 and the fourth link 114 are rotated on the first turning joint 115 to a direction of an arrow B.

When the fourth link 114 is rotated on the first turning joint 115 to a direction of an arrow B, the third link 113 is towed by the fourth link 114 and is moved to a direction of an arrow C, also, the second link 112 coupled to the third link 113 is towed by the third link 113 and is rotated on the second turning joint 116 to a direction of an arrow D, and at the same time, the second balancing link 122 which is extended from the fourth link 114 is also rotated to the direction of the arrow D, and the second counter weight 123 installed on the second balancing link 122 is moved to a direction of an arrow F.

At the same time, the first link 111 is pushed by the front link 119, which is rotated to the direction of the arrow A, is rotated on the second turning joint 116 to a direction of an arrow E, the first balancing link 121, which is extended from the first link 111, is rotated in connection with the first link 111 on the second turning joint 116 to a direction of an arrow E, and the first counter weight 123 installed on the first balancing link 121 is moved to a direction of an arrow G, and therefore, a torque generated in the second turning joint 116 according to the medical optical instrument M is compensated and a counter balancing of the stand 100 in which the medical optical instrument M is installed is always maintained stably regardless of a position of the medical optical instrument M.

Figure 2:
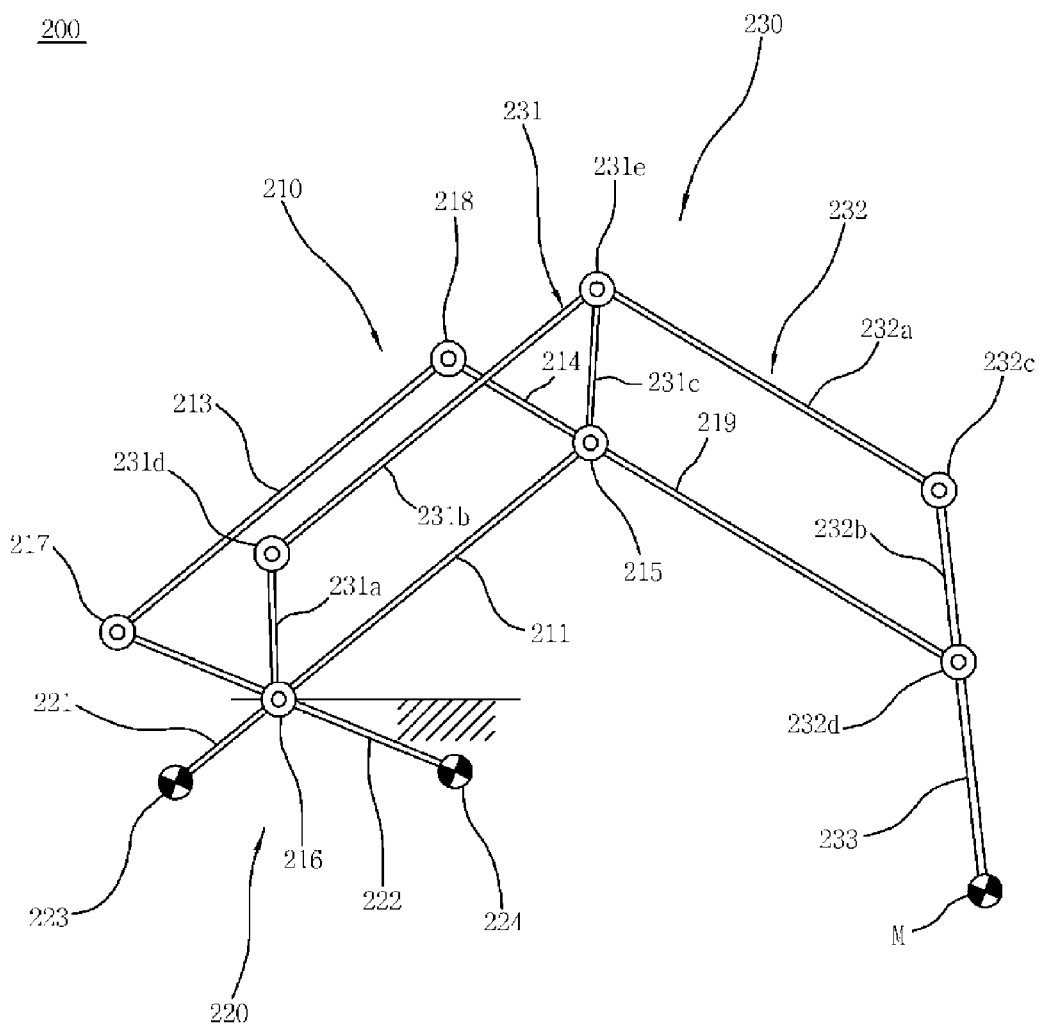
FIG. 2 is a figure showing a carrier arm for extension coupled to a carrier arm.
Figure 3:
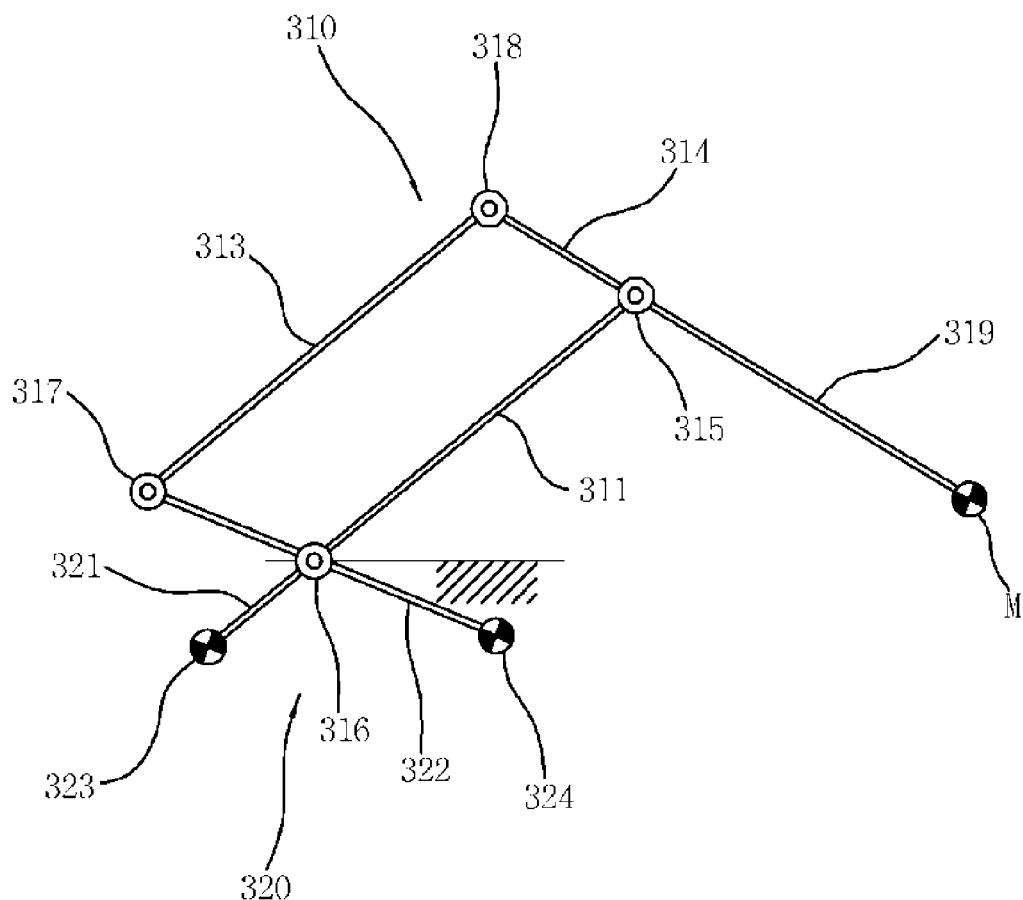
FIGS. 3-6, are figures showing a stepwise process of coupling a stand to a carrier arm for extension.
Figure 4:
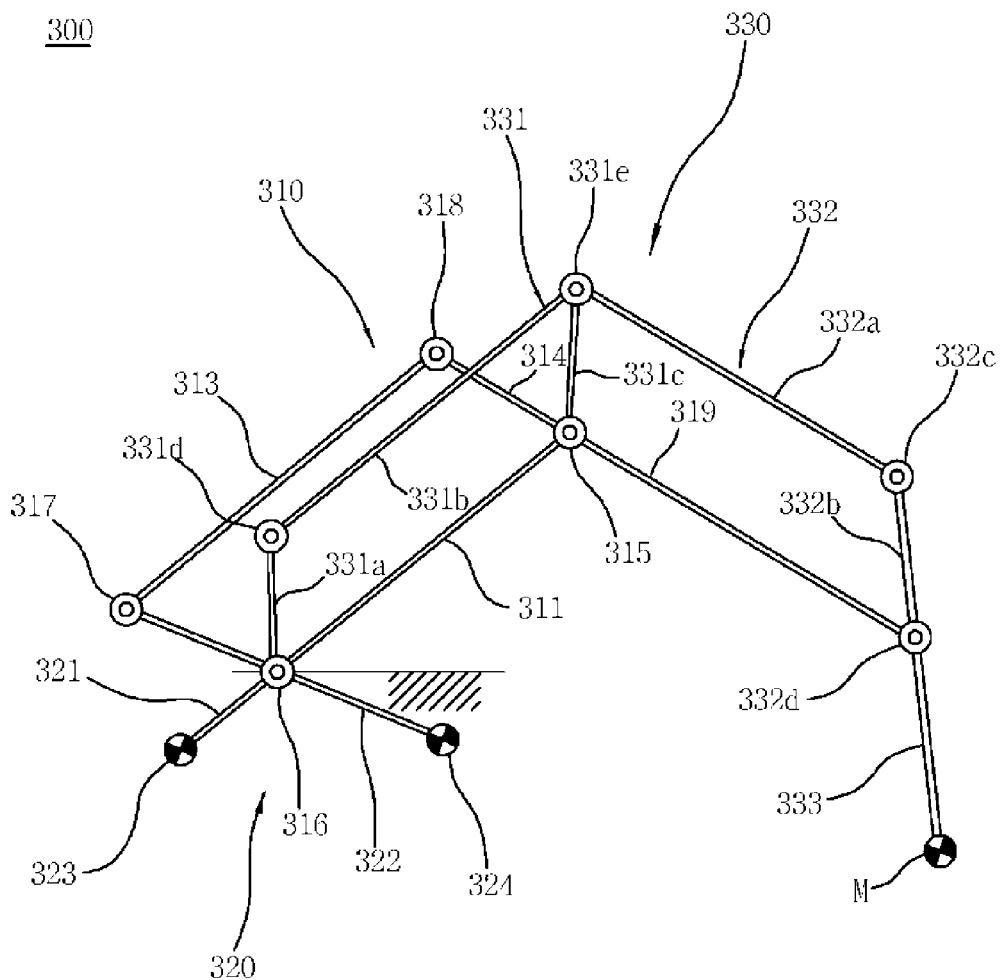

FIG. 2 is a figure showing a carrier arm for extension coupled to a carrier arm.

Referring to FIG. 2, a stand 200 according to another embodiment of the present invention may further include a carrier arm for extension 230 which is rotatably coupled to a carrier arm 210 to extend a length of the carrier arm 210.

When the carrier arm for extension 230 is coupled to the carrier arm 210, a medical optical instrument M is installed on a front link for extension 233 of the carrier arm for extension which will be described later.

The carrier arm for extension 230 may include a base link portion 231, an extension link portion 232, and a front link for extension 233.

The base link portion 231 is rotatably coupled to first and second turning joints 215 and 216 of the carrier arm 210 in a parallelogram shape.

For example, the base link portion 231 includes first to third links 231a 231b and 231c, and first and second turning joints 231d and 231e, the first to third links 231a 231b and 231c are rotatably coupled to each other by the first and second turning joints 231d and 231e, and the first link 231a and the third link 231c are rotatably coupled to the second and first turning joints 216 and 215 of the carrier arm 210, respectively. In more detail, the first link 231a is rotatably coupled to the second link 231b through the first turning joint 231d, the second link 231b is rotatably coupled to the third link 231c through the second turning joint 231e, the first link 231a is rotatably coupled to the carrier arm 210 through the second turning joint 216, the third link 231c is rotatably coupled to the carrier arm 210 through the first turning joint 215, and therefore, the base link portion 231 is rotatably coupled to the first and second turning joints 215 and 216 of the carrier arm 210 in a parallelogram shape.

The extension link portion 232 is rotatably coupled to the base link portion 231 and a front link 219 of the carrier arm 210 in a parallelogram shape. For example, the extension link portion 231 includes first and second links 232a and 232b, and a first turning joint 232c, the first and second links 232a and 232b are rotatably coupled to each other through the first turning joint 232c, and each of the first and second links 232a and 232b is rotatably coupled to the second turning joint 231e of the base link portion 231 and an end portion of the front link 119 of the carrier arm 210, respectively, through the turning joint 232d.

The front link for extension 233 is extended from the extension link portion 232. In more detail, the front link for extension 233 may be extended from the second link 232b of the extension link portion 232 to be parallel to the second link 232b of the extension link portion 232.

When the carrier arm for extension 230 is installed on the carrier arm 210 to extend a length of the stand 200, a medical optical instrument M is installed on the front link for extension 233 of the carrier arm for extension 230.

Since the extension link portion 232 is rotatably coupled to the front link 219 of the carrier arm 210 through the turning joint 232d, and if the medical optical instrument M installed on the front link 291 of the carrier arm 210 is moved, the front link 219 of the carrier arm 210, the front link for extension 233 rotated on the turning joint 232d to rotatably couple the second link 232b of the extension link portion 232 and the front link 219 of the carrier arm 210 according to the second link 232d, and the fourth link 214 are rotated on the first turning joint 215.

When the front link 219 of the carrier arm 210 and the fourth link 214 are rotated on the first turning joint 215, a third link 213 of the carrier arm is moved rotating a second link 212 and a second balancing link 222, then a second counter weight 224 is moved, and at the same time, a first link 211 of the carrier arm 210 and a first balancing link 221 are rotated on the a second turning joint 216 and a position of a first counter weight 223 is moved, and therefore, a torque generated in the second turning joint 216 according to the medical optical instrument M is compensated and a counter balancing of the stand 200 in which the medical optical instrument M is installed is always maintained stably regardless of a position of the medical optical instrument M.

FIGS. 3-6, are figures showing a stepwise process of coupling a stand to a carrier arm for extension.

Referring to FIGS. 3-6, carrier arms for extension 300 according to an embodiment of the present invention, N arms are rotatably coupled to each other, and at the same time, the N arms are rotatably and sequentially coupled to the carrier arm 310, and the carrier arm is extended for N-stages. Herein, N is natural number.

The carrier arm for extension 330, in order to extend a length of the stand 300, may include a base link portion 331, an extension link portion 332, an additional extension link portions 433 and 533, and a front links for extension 434 and 534.

The base link portion 331 is rotatably coupled to first and second turning joints 315 and 316 of the carrier arm 310 in a parallelogram shaped. Herein, a structure of the base link portion 331 is the same as the base link portion 231 of the carrier arm 230 shown in FIG. 2, thus, detailed explanation is omitted.

The extension link portion 332 is rotatably coupled to a front link 319 of the carrier arm 310 in a parallelogram shape. Also, a structure of the extension link portion 332 is the same as the extension link portion 232 of the carrier arm for extension 230 shown in FIG. 2 and detailed explanation is omitted.

The additional extension link portions 433 and 533 are rotatably coupled to an extension link portions 432 and 532 of remaining carrier arms 430 and 530 except for the carrier arm for extension 330 which is coupled to the carrier arm 310 to a first order, and N−1 arms are serially and rotatably coupled to the carrier arm for extension which is coupled to the carrier arm 310 to an N-th order.

The additional extension link portions 433 and 533 may include a first links 433a 533a and 533e, a second links 433b 533b and 533f, and a first turning joints 433c 533c and 533g. The first and second links 433a 533a 533e 433b 533b and 533f are coupled to each other through the first turning joints 433c 533c and 533g. The first links 433a 533a and 533e may be rotatably coupled to the first turning joints 432c and 532c of the extension link portions 432 and 532 or to a first turning joint 533c of another neighboring additional extension link portion 533A (the first link 433a and 533a are coupled to the first turning joints 432c and 532c, and the first link 533e is coupled to a first turning joint 533c of another neighboring additional extension link portion 533A). The second links 433b 533b and 533f may be rotatably coupled to a front links 334 434 and 534 of neighboring carrier arms for extension 330 430 and 530. In other words, the second links 433b 533b and 533f of the additional extension link portions 433 and 533, which are included in the Nth carrier arm for extension rotatably coupled to the carrier arm 310 to an N-th order, are rotatably coupled to the front links for extension 334 and 434 of the carrier arms 330 and 430 which are rotatably and coupled to the carrier arm 310 to an N-th order.

Figure 5:
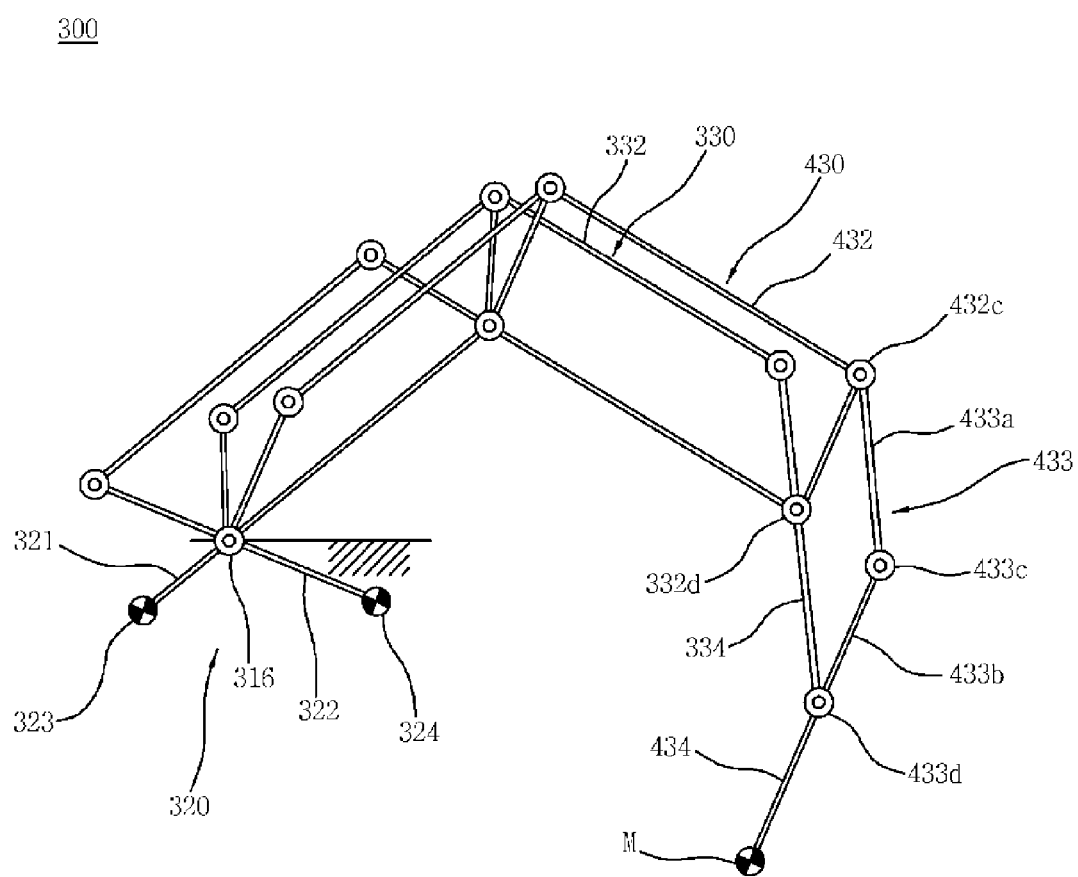
Figure 6:
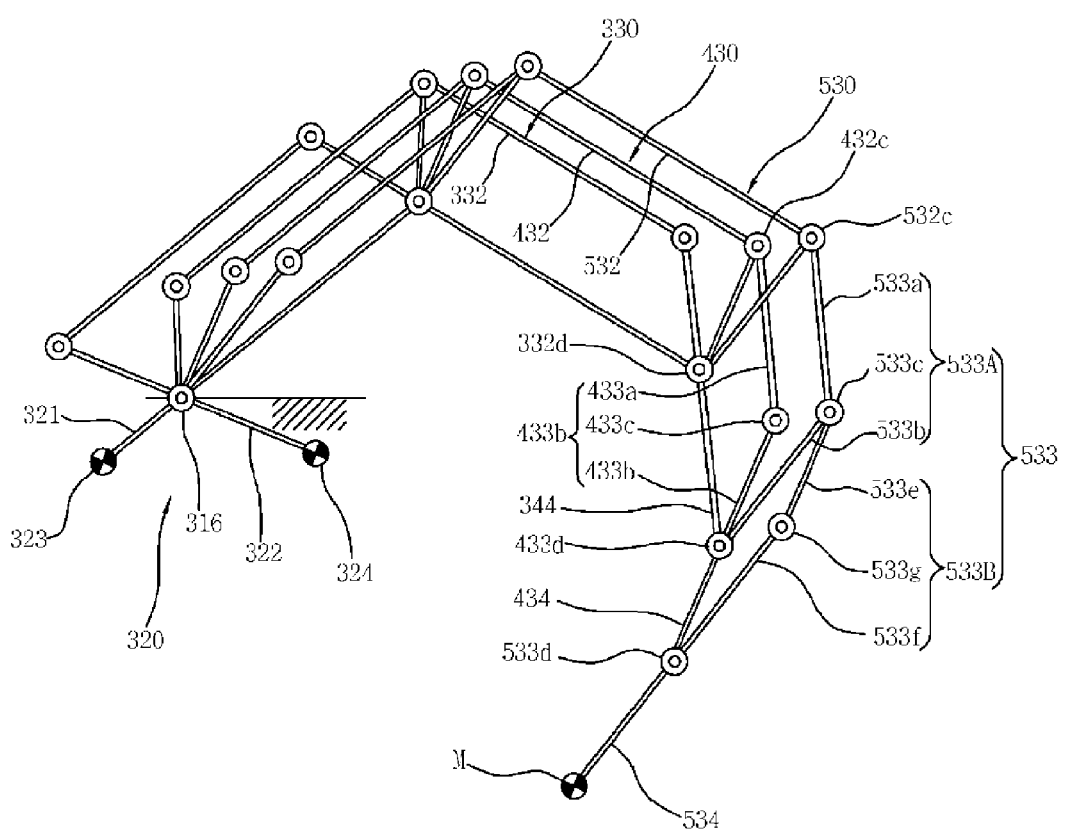

Explaining in more detail the additional extension link portions 433 and 533, the additional extension link portion 433 and 533 is not coupled to the carrier arm for extension 330 which is coupled to the carrier arm 310 to a first order as shown in FGI. 4, the additional extension link portions 433 and 533 are coupled from the carrier arm for extension 430, which is coupled to the carrier arm 310 to a second order, to the Nth carrier arm for extension which is coupled to the carrier arm 310 to an N-th order as shown in FIGS. 5-6.

As shown in FIG. 5, only the first additional extension link portion 433 is rotatably coupled to the second carrier arm for extension 430 which is coupled to the carrier arm 310 to a second order. In other words, the first link 433a and the second link 433b of the first additional extension link portion 433 are rotatably coupled to each other through the first turning joint 433c, the first link 433a is rotatably coupled to the extension link portion 332 and, the second link 433b is rotatably coupled to the front link for extension 334 of the first carrier arm for extension 330 which is rotatably coupled to the carrier arm to a first order.

Also, as shown in FIG. 6, in a carrier arm for extension 530 which is coupled to the carrier arm 310 to a third order, the first and second additional extension link portions 533A and 533B are rotatably and serially coupled to each other, and the first and second additional extension link portions 533A and 533B are rotatably coupled to the extension link portion 532. In other words, the first link 533e of the second additional extension link portion 533B is rotatably coupled to the first turning joint 533c of the first additional extension link portion 533A and the first and second additional extension link portions are serially coupled, the first link 533a of the first additional extension link portion 533a, the second link 533b of the first additional extension link portion 533A is rotatably coupled to the front link for extension 334 of the first carrier arm for extension 330, and the second link 533f of the second additional extension link portion 533B is rotatably coupled to the front link for extension 434 of the second carrier arm for extension 430.

In other words, the additional extension link portions 433 and 533 are rotatably coupled to the extension link portion of the remaining carrier arms for extension except for the first carrier arm for extension 330 which is coupled to the carrier arm 310 to a first order, N−1 arms are serially and rotatably coupled to each other to the carrier arm for extension is coupled to an N-th order, and a length of the stand 300, which is rotatably coupled to the extension link portion, is extended.

The front links for extension 334 434 and 534 may be extended from the extension link potion 332 of the first carrier arm for extension 330 which is coupled to the carrier arm 310 to first order and the additional extension link portions 433 and 533 positioned at the end portion of the remaining carrier arms for extension 430 and 530.

Among the front links for extension 334 434 and 534 as described above, except for front link for extension 534 of the carrier arm for extension 530 coupled to the carrier arm 310 to the last, the front links for extension 334 and 434 of the Nth carrier arms for extension 330 and 430 which is coupled to the carrier arm 301 to an N-th order may be rotatably coupled to the second links 433b and 533f of the N-th additional extension link portions 433 and 533B of the carrier arm for extension 430 and 530 in which the carrier arm for extension 430 and 530 are coupled to the carrier arm 310 to the N+1-th.

Referring to FIG. 6, the front link for extension 434 of the second carrier arm for extension 430 which is coupled to the carrier arm 310 to the second is rotatably coupled to the second link 533f of the second additional extension link portion 533B of the third carrier arm for extension 530 which is coupled to the carrier arm 310 to a third order, the front link for extension 334 of the first carrier arm for extension 330 which is coupled to the carrier arm 310 to a first order is rotatably coupled to the second link 433b of the first additional extension link portion 433 of the second carrier arm for extension 430 which is coupled to the carrier arm 310 to a second order.

As shown in FIGS. 3-6, when N carrier arms for extension 330 430 and 530 are sequentially coupled to the carrier arm 310, except for the front link for extension 534 of the is carrier arm for extension 530 which is coupled to the carrier arm 310 to the last, the front links for extension 334 and 434 of the Nth carrier arms for extension 330 and 430 which is coupled to the carrier arm 310 to an N-th order may be rotatably coupled to the second links 433b and 533f of the N-th additional extension link portions 433 and 533 of the carrier arm for extension 430 and 530 in which the carrier arm for extension 430 and 530 are coupled to the carrier arm 310 to the N+1-th, therefore, when a position of the medical optical instrument M installed on the front link for extension 534 of the coupled carrier arm for extension 530 to the last is moved, the first and second counter weights 323 and 324 are moved in connection with the medical optical instrument M, and therefore, a torque generated from the second turning joint 316 according to the medical optical instrument M is compensated and a counter balancing of the stand 300 in which the medical optical instrument M is installed is always maintained stably regardless of a position of the medical optical instrument M.

In other words, when the medical optical instrument is moved, the second link 533f of the extension link portion 532 of the carrier arm for extension 530 coupled to an N-th order and the second link 332b of the extension link portion 332 of the first carrier arm for extension 330 which is coupled to the carrier arm 310 for extension to a first order to the front link for extension 334 are rotated on the turning joints 332d 433d and 533d.

Also, the front link for extension 334 of the first carrier arm for extension 330 and the front link 319 of the carrier arm 310 are rotated on the first turning joint 315, the first and second balancing links 321 and 322 are rotated on the second turning joint 316 of the carrier arm 310 and, position of the first and second counter weights 323 and 324 are moved, and therefore, a torque generated in the second turning joint 316 according to the medical optical instrument M is compensated and a counter balancing of the stand 300, in which the medical is optical instrument M is installed, is always maintained stably regardless of a position of the medical optical instrument M.

As described above, a stand for medical optical instrument according to an embodiment of the present invention is capable of installing first and a second counter weights 123 and 124 to be replaceable according to a weight of medical optical instrument which is installed on a carrier arm, as well as, when a position of medical optical instrument is changed, a counter balance of weight according to a changed weight of a medical optical instrument is easily adjusted by moving first and second counter weights 123 and 124 in which first and second balancing link 121 and 122 of carrier arm 110 are rotated in connection with the medical optical instrument on a second turning joint 116. And, there is an effect of maintaining a counter balancing completely stable in both sides, horizontal direction and vertical direction, regardless of a position of a medical optical instrument.

Also, even though a length of a stand is extended to a user's desired length by using carrier arms for extension 330 430 and 530, a front link 319 of carrier arm 310 and front links for extension 334 and 434 of carrier arms for extension 330 and 430 are organically coupled to the neighboring carrier arms for extension 330 430 and 530, a movement of front link for extension 534 positioned at the most end is transferred to first and second balancing links 321 and 322 through passing first and second links 311 and 312 of carrier arm 310, positions of the first and second counter weights 323 and 324 are moved according to a changed position of a medical optical instrument, and therefore, a complete and stable counterbalancing on both sides, horizontal and vertical directions, is maintained regardless of position of a medical optical instrument.

In other words, a length of a stand is easily extended to a user's desired length, as well as, easy counter balancing and maintaining stably a counter balancing are capable when the length of the stand is extended.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. A stand for medical optical instrument comprising:
   a carrier arm including a first to fourth links rotatably coupled in a parallelogram shape with a first to fourth turning joints, wherein the second turning joint is rotatably coupled to a holding unit, and a front link extended from the fourth link; and
   a counter balancing unit coupled to the first and second links to maintain a counter balancing of the carrier arm by compensating a torque, which is generated in the second turning joint by a medical optical instrument installed on the front link, by rotating in connection with the first and second links on the second turning joint according to the rotation of the carrier arm,
   wherein the counter balancing unit comprises:
   first and second balancing links extended from the first and second links, respectively, to rotate in connection with the first and second links on the second turning joint; and
   first and second counter weights installed on the first and second balancing links, respectively.

2. The stand for medical optical instrument of claim 1, wherein lengths of the first and second balancing links are changeable according to a weight of the medical optical instrument.

3. The stand for medical optical instrument of claim 1, wherein the first and second counter weights are installed on the first and second balancing links, respectively, to be replaceable according to a weight of the medical optical instrument.

4. The stand for medical optical instrument of claim 1, further comprising a carrier arm for extension rotatably coupled to the carrier arm to extend a length of the carrier arm.

5. The stand for medical optical instrument of claim 4, wherein the carrier arm for extension comprises:
   a base link portion rotatably coupled to the first and second turning joints of the carrier arm in a parallelogram shape;
   an extension link portion rotatably coupled to the base link portion and the front link of the carrier arm in a parallelogram shape; and
   a front link for extension extended from the extension link portion.

6. The stand for medical optical instrument of claim 4, wherein the carrier arm for extension has N arms rotatably coupled to each other, and sequentially and rotatably coupling to the carrier arm to extend the carrier arm by N-steps.

7. The stand for medical optical instrument of claim 6, wherein the carrier arm for extension comprises:
   a base link portion rotatably coupled to the first and second turning joints of the carrier arm in a parallelogram shape;
   an extension link portion rotatably coupled to the base link portion and the front link of the carrier arm in a parallelogram shape;
   an additional extension link portion rotatably coupled to the extension link portions of the remaining carrier arms for extension except for the carrier arm for extension coupled to the carrier arm to a first order, wherein the carrier arm for extension coupled to the carrier arm to an N-th order, in which N−1 additional extension link portions are rotatably and serially coupled to the carrier arm for extension coupled to the carrier arm to an N-th order, is rotatably coupled to the extension link portion; and a front link for extension extended from the extension link portion of the carrier arm for extension which is coupled to the carrier arm to the first and the additional extension link portion which is positioned at the end of the remaining carrier arms for extension, wherein, the front link for extension of the carrier arm for extension, which is coupled to the carrier arm to an N-th order, except for the front link of the carrier arm for extension which is coupled to the carrier arm to the last, is rotatably coupled to the additional extension link portion of the carrier arm for extension which is coupled to the carrier arm to an N+1-th order.

\* \* \* \* \*